US011426186B2

(12) United States Patent
Brouillette et al.

(10) Patent No.: US 11,426,186 B2
(45) Date of Patent: Aug. 30, 2022

(54) CATHETER DEVICE FOR DELIVERING MECHANICAL WAVES

(71) Applicant: Les Solutions Medicales Soundbite Inc., Saint-Laurent (CA)

(72) Inventors: Martin Brouillette, Sherbrooke (CA); Louis-Philippe Riel, Montreal (CA); Steven Dion, Sherbrooke (CA); Dustin Arless, Vaudreuil-Dorion (CA); Simon Berube, Sherbrooke (CA); Philippe Lacasse, Sherbrooke (CA)

(73) Assignee: Les Solutions Médicales Soundbite Inc., Saint-Laurent (CA)

( * ) Notice: Subject to any disclaimer, the term of this patent is extended or adjusted under 35 U.S.C. 154(b) by 372 days.

(21) Appl. No.: 16/342,746

(22) PCT Filed: Oct. 26, 2017

(86) PCT No.: PCT/IB2017/056675
§ 371 (c)(1),
(2) Date: Apr. 17, 2019

(87) PCT Pub. No.: WO2018/078568
PCT Pub. Date: May 3, 2018

(65) Prior Publication Data
US 2020/0268397 A1    Aug. 27, 2020

Related U.S. Application Data

(60) Provisional application No. 62/413,032, filed on Oct. 26, 2016, provisional application No. 62/426,392, (Continued)

(51) Int. Cl.
*A61B 17/22* (2006.01)
*A61B 90/00* (2016.01)
*A61B 17/32* (2006.01)

(52) U.S. Cl.
CPC .............. *A61B 17/22012* (2013.01); *A61B 2017/22017* (2013.01); *A61B 2017/22038* (2013.01);
(Continued)

(58) Field of Classification Search
CPC .......... A61B 17/221; A61B 17/22012; A61B 17/22022; A61B 17/22004;
(Continued)

(56) References Cited

U.S. PATENT DOCUMENTS 5,480,382 A * 1/1996 Hammerslag ..... A61M 25/0053
600/585
2014/0052145 A1   2/2014 Adams et al.
2015/0250966 A1 * 9/2015 Shabat ............. A61M 16/0486
128/200.26

FOREIGN PATENT DOCUMENTS

DE  2438648 A1  2/1976
EP  0702935 A1  3/1996
(Continued)

OTHER PUBLICATIONS

International Search Report; Canadian Intellectual Property Office; International Application No. PCT/IB2017/056675; dated Feb. 26, 2018; 3 pages.
(Continued)

*Primary Examiner* — Vi X Nguyen
(74) *Attorney, Agent, or Firm* — Taft Stettinius & Hollister LLP

(57) ABSTRACT

A catheter device including an internal elongated and hollow body extending between a proximal end and a distal end along a longitudinal axis, the internal elongated and hollow body defining a longitudinal aperture that extends between the proximal and distal ends thereof, the longitudinal aperture being shaped and sized for receiving a guide wire
(Continued)

therein, and at least one mechanical waveguide secured to the internal elongated and hollow body and extending longitudinally along at least a portion of the internal elongated and hollow body, with the at least one mechanical waveguide capable of propagating at least one mechanical wave therealong.

27 Claims, 8 Drawing Sheets

Related U.S. Application Data filed on Nov. 25, 2016, provisional application No. 62/429,122, filed on Dec. 2, 2016.

(52) U.S. Cl.
CPC .............. *A61B 2017/22079* (2013.01); *A61B 2017/320088* (2013.01); *A61B 2090/3966* (2016.02); *A61B 2217/007* (2013.01)

(58) Field of Classification Search
CPC ........... A61B 2017/22017; A61B 2017/22038; A61B 2017/320088
See application file for complete search history.

(56) References Cited

FOREIGN PATENT DOCUMENTS

| JP | 62268547 A | 11/1987 |
| WO | 9204933 A1 | 4/1992 |
| WO | 199204933 A | 4/1992 |
| WO | 2011050085 A2 | 4/2011 |
| WO | 2014004887 A1 | 1/2014 |

OTHER PUBLICATIONS

Written Opinion of the International Searching Authority; Canadian Intellectual Property Office; International Application No. PCT/IB2017/056675; dated Feb. 26, 2018; 5 pages.

Extended European Search Report; European Patent Office; European Patent Application No. 17865695.5; dated May 7, 2020; 8 pages.

Communication Pursuant to Article 94(3) EPC; European Patent Office; European Application No. 17865695.5; dated Mar. 29, 2022; 4 pages.

* cited by examiner

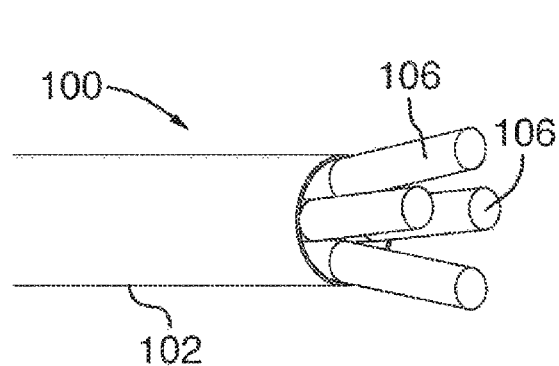
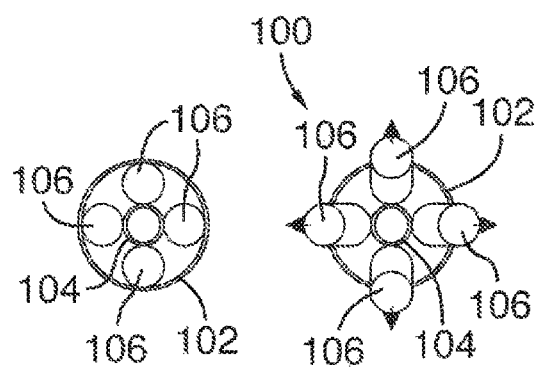
FIG.6a    FIG.6b    FIG.6c
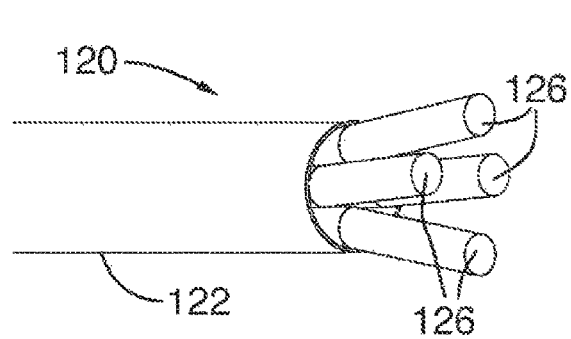
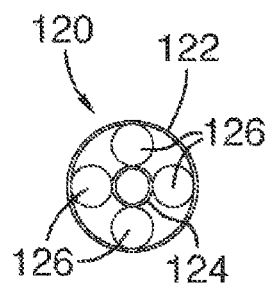
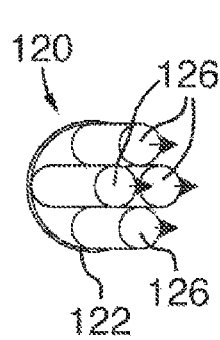
FIG.7a    FIG.7b    FIG.7c

CATHETER DEVICE FOR DELIVERING MECHANICAL WAVES

CROSS REFERENCE TO RELATED APPLICATIONS

This application is a U.S. National Phase of International PCT Application No. PCT/IB2017/056675 filed Oct. 26, 2017, which claims the benefit of U.S. Provisional Patent Application No. 62/413,032 filed Oct. 26, 2016, U.S. Provisional Patent Application No. 62/426,392 filed Nov. 25, 2016, and U.S. Provisional Patent Application No. 62/429,122 filed Dec. 2, 2016, the contents of each application hereby incorporated by reference in their entirety.

TECHNICAL FIELD

The present invention relates to the field of medical catheters, and more particularly to catheters adapted for delivering shock waves to perform medical treatment on cells, tissues or organs.

BACKGROUND

Non-invasive therapies using ultrasound or shock waves are commonly used to treat a variety of medical conditions such as kidney stones and prostate cancer. Such therapy methods or procedures are attractive because the source of mechanical waves is located outside the body of the patient to be treated and delivered through the skin. Therefore, such a procedure can be said to be non-invasive. By adequately designing the mechanical energy source, the delivered energy can be focused on a target to be treated within the body. However, there are limitations to these techniques. For example, the exact location of the target may be difficult to obtain due to limitations of the imaging method used. Also, the energy may not be focused at the exact desired location due to physical limitations of the focusing wave itself and heterogeneities within the various tissues and organs through which the wave must propagate. Finally, the energy density at the target may not be sufficient to accomplish the desired treatment.

Therefore there is a need for an improved method and device for delivering shock waves to target cells, tissues or organs.

SUMMARY

According to a broad aspect, there is provided a catheter device comprising: an internal elongated and hollow body extending between a proximal end and a distal end along a longitudinal axis, the internal elongated and hollow body defining a longitudinal aperture that extends between the proximal and distal ends thereof, the longitudinal aperture being shaped and sized for receiving a guide wire therein; and at least one mechanical waveguide secured to the internal elongated and hollow body and extending longitudinally along at least a portion of the internal elongated and hollow body, the at least one mechanical waveguide for propagating at least one mechanical wave therealong.

In one embodiment, the catheter device further comprises an external elongated and hollow body defining a cavity, the internal elongated and hollow body and the at least one mechanical waveguide being inserted into the cavity, the at least one mechanical waveguide being positioned between the internal elongated and hollow body and the external elongated and hollow body.

In one embodiment, the catheter device further comprises at least one plate outwardly projecting from an outer face of the internal elongated and hollow body each at a respective position along a length of the internal elongated and hollow body, each one of the at least one plate comprising at least one waveguide receiving aperture therethrough, each one of the at least one waveguide receiving aperture having a respective one of the at least one mechanical waveguide inserted therein.

In one embodiment, each one of the at least one plate is integral with the internal elongated and hollow body.

In another embodiment, each one of the at least one plate is independent from the internal elongated and hollow body and fixedly secured thereto, each one of the at least one plate having a main aperture in which the internal elongated and hollow body is inserted.

In one embodiment, the at least one waveguide receiving aperture comprises a plurality of waveguide receiving apertures.

In one embodiment, the waveguide receiving apertures are arranged according to at least one row.

In one embodiment, on each one of the at least one plate, the waveguide receiving apertures are symmetrically positioned.

In another embodiment, on each one of the at least one plate, the waveguide receiving apertures are asymmetrically positioned.

In one embodiment, the at least one plate comprises a plurality of plates.

In one embodiment, a position of a given one of the plurality of waveguide receiving apertures in which a same one of the at least one mechanical waveguide is inserted varies from one of the plurality of plates to another one of the plurality of plates.

In one embodiment, a distance between a center of the internal elongated and hollow body and a center of the waveguide receiving apertures varies along a length of the internal elongated and hollow body.

In one embodiment, a distance between adjacent ones of the plurality of plates is constant along the internal elongated and hollow body.

In another embodiment, a distance between adjacent ones of the plurality of plates varies along the internal elongated and hollow body.

In one embodiment, the at least one plate has one of a circular, square, rectangular, triangular, and hexagonal shape.

In one embodiment, the at least one waveguide receiving aperture has one of a circular, square, rectangular, triangular, and hexagonal shape.

In one embodiment, the at least one plate is made of an acoustically insulating material.

In one embodiment, the catheter device further comprises at least one acoustically insulating body each inserted around a respective one of the at least one mechanical waveguide.

In one embodiment, each one of the at least one mechanical waveguide is provided with a respective one of the at least one acoustically insulating body.

In one embodiment, the at least one acoustically insulating body each comprises at least one wire each wrapped around a respective one of the at least one mechanical waveguide.

In one embodiment, the at least one wire has a helical shape to form a helical winding around the respective one of the at least one mechanical waveguide.

In one embodiment, an axial pitch of the helical winding is constant along a length of the respective one of the at least one mechanical waveguide.

In another embodiment, an axial pitch of the helical winding varies along a length of the respective one of the at least one mechanical waveguide.

In one embodiment, the axial pitch is greater than a cross-sectional dimension of the at least one wire.

In one embodiment, the at least one wire is made of an acoustically insulating material.

In one embodiment, the at least one wire is provided with one of a circular, square, rectangular, triangular and hexagonal cross-sectional shape.

In one embodiment, the at least one acoustically insulating body comprises at least one mesh each inserted around a respective one of the at least one mechanical waveguide.

In one embodiment, a pattern of the at least one mesh is constant along the respective one of the at least one mechanical waveguide.

In another embodiment, a pattern of the at least one mesh varies along the respective one of the at least one mechanical waveguide.

In one embodiment, the at least one acoustically insulating body extends along at least a longitudinal section of the respective one of the at least one mechanical waveguide.

In one embodiment, a given section of the respective one of the at least one mechanical waveguide is uncovered by the at least one acoustically insulating body.

In one embodiment, the at least one acoustically insulating body is made of an acoustically insulating material.

In one embodiment, the external elongated and hollow body is flexible so as to correspond to a sheath.

In one embodiment, a distal end of the at least one mechanical waveguide is movable along the longitudinal axis relative to the distal end of the internal elongated and hollow body.

In one embodiment, a distal end of the at least one mechanical waveguide is further one of radially and laterally movable relative to the distal end of the external elongated and hollow body.

In one embodiment, the catheter device further comprises at least one arm extending between the internal elongated and hollow body and the external elongated and hollow body.

In one embodiment, the at least one arm is made of an acoustically insulating material.

In one embodiment, at least one of the internal elongated and hollow body and the external elongated and hollow body is made of an acoustically insulating material.

In one embodiment, at least one of the internal elongated and hollow body and the external elongated and hollow body is made of one of a polymer and a graded polymer.

In one embodiment, at least one of the external elongated and hollow body, the internal elongated and hollow body and the at least one mechanical waveguide has a circular cross-sectional shape.

In one embodiment, the at least one mechanical waveguide comprises a plurality of mechanical waveguides.

In one embodiment, the mechanical waveguides are symmetrically positioned around the internal elongated and hollow body.

In one embodiment, the mechanical waveguides are arranged according to at least one row of waveguides around the internal elongated and hollow body.

In one embodiment, the catheter device further comprises at least one tube inserted within the external elongated and hollow body.

In one embodiment, the at least one tube is adapted to blow a fluid at a distal end thereof.

In another embodiment, the at least one tube is adapted to aspirate at least one of a fluid and debris from a distal end thereof.

In one embodiment, the external elongated and hollow body comprises a mesh sleeve.

In one embodiment, the at least one mechanical waveguide has a distal beveled end.

In one embodiment, the at least one mechanical waveguide is provided with one of a circular, square, rectangular, triangular and hexagonal cross-sectional shape.

In one embodiment, a distal end of the at least one mechanical waveguide is coplanar with the distal end of the internal elongated and hollow body.

In another embodiment, a distal end of the at least one mechanical waveguide projects forwardly from the distal end of the internal elongated and hollow body.

In one embodiment, the at least one mechanical waveguide is movable relative to the internal elongated and hollow body.

In one embodiment, a cross-sectional shape of the longitudinal aperture is one of circular, square, rectangular and hexagonal.

In one embodiment, a cross-sectional shape of the external elongated and hollow body is one of circular, square, rectangular and hexagonal.

In one embodiment, the catheter device further comprises a radiopaque element.

In one embodiment, the radiopaque element comprises a radiopaque ring.

In one embodiment, the radiopaque ring is secured to the external elongated and hollow body.

In one embodiment, the catheter device further comprises a drug capsule positioned at the distal end of the at least one mechanical waveguide.

For the purpose of the present description, a mechanical wave should be understood as a signal having arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of $1/fc$.

In one embodiment, the mechanical pulse has a center frequency fc comprised between about 20 kHz and about 10 MHz. In one embodiment, the amplitude of the mechanical pulse when reaching the distal end of the catheter device is comprised between about 10 MPa and about 1000 MPa. In one embodiment, the duration of the mechanical pulse when reaching the distal end of the catheter device is in the order of $1/fc$.

In one embodiment, the amplitude of a mechanical pulse when reaching the distal end of the catheter device is comprised between about 10 MPa and about 1000 MPa.

BRIEF DESCRIPTION OF THE DRAWINGS

Further features and advantages of the present invention will become apparent from the following detailed description, taken in combination with the appended drawings, in which:

FIG. 6a is a side view of a catheter device comprising a sheath, a central catheter and four mechanical waveguides inserted between the sheath and the central catheter, the mechanical waveguides being movable radially and outwardly away from the sheath, in accordance with an embodiment;

FIG. 6b is a front view of the catheter device of FIG. 6a when the mechanical waveguides are in a retracted position:

FIG. 6c is a front view of the catheter device of FIG. 6a when the mechanical waveguides are in an extended position;

FIG. 7a is a side view of a catheter device comprising a sheath, a central catheter and four mechanical waveguides inserted between the sheath and the central catheter, the mechanical waveguides being movable laterally and outwardly away from the sheath, in accordance with an embodiment;

FIG. 7b is a front view of the catheter device of FIG. 7a when the mechanical waveguides are in a retracted position;

FIG. 7c is a front view of the catheter device of FIG. 7a when the mechanical waveguides are in an extended position;

FIG. 11b is a partial cross-sectional view of the plate of FIG. 11a;

It will be noted that throughout the appended drawings, like features are identified by like reference numerals.

DETAILED DESCRIPTION

Figure 1:
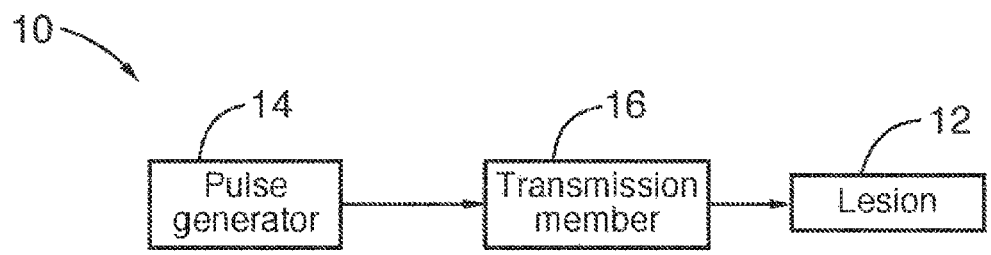
FIG. 1 is a block diagram illustrating a system for treating a lesion, in accordance with an embodiment.

FIG. 1 illustrates one embodiment of a system 10 for treating a lesion 12 to order to describe a particular context in which the present catheter is to be used. The system 10 comprises a pulse generator 14 and a transmission member 16 adapted to propagate mechanical waves or pulses.

The pulse generator 14 is adapted to generate a mechanical wave such as a high amplitude and short duration mechanical pulse. The pulse generator 14 may comprise at least one broadband source and/or at least one narrow band source. The narrow or broad band source may be an electromechanical transducer. The pulse generator 14 may comprise a spatial concentrator to focus the output of at least one source toward a focal zone at which the proximal end of the transmission member 16 is located so as to couple the generated mechanical pulse therein.

The transmission member 16 such as a mechanical waveguide extends between a first or proximal end that is operatively connected to the pulse generator 14 and a second or distal end. The transmission member 16 is adapted to receive mechanical pulses at its proximal end and propagate the mechanical pulses up to its distal end. When it reaches the distal end, the mechanical pulse is at least partially transmitted to generate a transmitted pulse that propagates outside of the transmission member 16. It should be understood that a pulse may also be reflected by the distal end and propagates back in the transmission member 16 towards the proximal end thereof. The transmitted mechanical pulse corresponds to a mechanical pulse that propagates in the medium surrounding the distal end of the transmission member 16 up to the lesion 12. The transmitted pulse further propagates into the lesion 12, which may create cracks within the lesion 12, and eventually cleaves or breaks the lesion 12 into pieces.

In an embodiment in which the distal end of the transmission member 16 abuts against the lesion 12, the mechanical waveguide 16 may further be used to break the lesion 12 and/or drill a hole into the lesion 12. The transmission of the mechanical pulse at the distal end of the transmission member 16 creates a movement of the distal end of the transmission member 16. This movement may be along the longitudinal axis of the transmission member 16. Alternatively, the movement may be perpendicular to the longitudinal axis or it may be a combination of movements both along the longitudinal axis and perpendicular to the longitudinal axis of the transmission member. During this movement, the distal end of the transmission member 16 nominally first moves towards the lesion 12 and then moves back into its initial position. It should be understood that the movement may be inverted (i.e., the distal end may first move away from the lesion 12 and then towards the lesion 12) depending on the polarity of the mechanical pulse reaching the distal end of the transmission member 16. When a plurality of distinct mechanical pulses are successively transmitted at the distal end of the transmission member 16, the movement of the distal end may be seen as a jack-hammer movement which may be used to treat the lesion 12.

Figure 2:
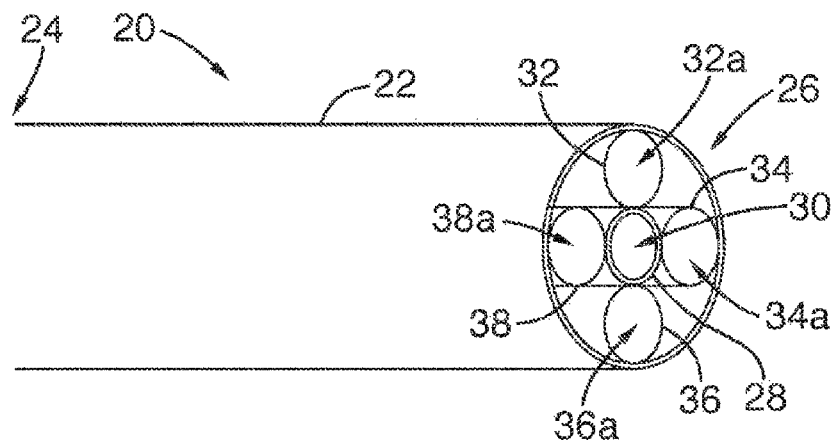
FIG. 2 illustrates a catheter device comprising a sheath, a central catheter and four mechanical waveguides inserted between the sheath and the central catheter and arranged evenly around the circumference of the central catheter, in accordance with an embodiment.

FIG. 2 illustrates one embodiment of a catheter device or assembly 20 which may be used as a transmission member such as the transmission member 16 of FIG. 1 for propagating mechanical waves or pulses coming from an extracorporeal mechanical energy source.

The catheter device 20 comprises an elongated and hollow body or sleeve 22 which extends between a proximal end 24 and a distal end 26. The catheter device 20 may also comprise a catheter or guiding elongated and hollow body 28 which is inserted into the body 22 and extends between a proximal end (not shown) and a distal end 30. The guiding body 28 is hollow so as to allow a guide wire to extend therethrough from its proximal end to its distal end 30. The catheter 20 further comprises four mechanical waveguides 32, 34, 36 and 38 which are each inserted into the body 22 between the body 28 and the body 22 and each extend between a proximal end (not shown) and a distal end 32a, 34a, 36a and 38a, respectively. The mechanical waveguides 32, 34, 36 and 38 are designed so that mechanical waves or pulses may propagate therealong.

In one embodiment, the catheter device 20 further comprises at least one arm extending radially between the catheter 28 and the internal face of the body 22 for securing the catheter 28 and the body 22 together. In one embodiment, the arm is made of an acoustically insulating material. In another embodiment, the catheter 28 and the mechanical waveguides 32, 34, 36 and 38 are maintained in position into the body 22 via compression forces. In this case, when inserted within the body 22, the mechanical waveguides 32-38 are in physical contact with the external face of the catheter 28 and the internal face of the body 22. The internal diameter of the body 22 substantially corresponds to the summation of the external diameter of the catheter 28 and twice the diameter of the mechanical waveguides 32-38.

In one embodiment, the body 22 may be omitted. In this case, the mechanical waveguides 32, 34, 36 and 38 are secured to the catheter 28. It should be understood that any adequate method for securing the mechanical waveguides 32, 34, 36 and 38 to the catheter 28 may be used. For example, the mechanical waveguides 32, 34, 36 and 38 may be glued to the catheter 28. In another example, a wire may be wrapped around the mechanical waveguides 32, 34, 36 and 38 for securing the mechanical waveguides 32, 34, 36 and 38 to the catheter 28.

In one embodiment, the body 22 may be made of a flexible material to correspond to a sheath. In one embodiment, the body 22 may be made of an acoustically insulating material. In one embodiment, the body 22 may be a single or a plurality of smaller diameter wires.

In use, a guide wire is inserted into the patient so as to cross the lesion to be treated or be adjacent the lesion. Then the proximal end of the guide wire is inserted into the distal end 26 of the catheter 28 and the catheter device 20 is inserted into the patient body. The guide wire is then used for guiding the movement of the catheter device 20 up to the lesion to be treated by sliding the catheter device 20 along the guide wire. When the catheter device 20 is adequately positioned relative to the lesion to be treated, mechanical pulses are generated and propagated along the mechanical waveguides 32, 34, 36 and 38 to treat the lesion.

While in the illustrated embodiment the distal ends of the mechanical waveguides 32, 34, 36 and 38 are coplanar with the distal end 26 of the body 22 and the distal end of the catheter 28, it should be understood that other configurations may be possible. For example, the distal ends of the mechanical waveguides 32, 34, 36 and 38 may project from the distal end 26 of the body 22 and/or the distal end of the catheter 28. In another example, the distal end of the body 22 and/or the distal end of the catheter 28 may project from the distal ends of the mechanical waveguides 32, 34, 36 and 38. In a further example, the distal end of some of the mechanical waveguides 32, 34, 36 and 38 may project from the distal end of the body 22 while the other mechanical waveguides 32, 34, 36 and 38 may have a distal end which is coplanar with that of the body 22.

While the catheter device 20 comprises four mechanical waveguides 32, 34, 36 and 38, it should be understood that the number of mechanical waveguides inserted into the body 22 may vary as long as the catheter device 20 comprises at least one mechanical waveguide. Similarly, the shape, dimensions and position within the body 22 of the mechanical waveguides may vary.

While in FIG. 2 the catheter 28 and the body are concentric, it should be understood that other configurations may be possible. For example, the mechanical waveguide(s) located on one side of the catheter 28 may have a larger diameter than the mechanical waveguide(s) located on the opposite side of the catheter so that the catheter 28 is not centered on the central longitudinal axis of the body 22.

While in the illustrated embodiment, the body 22, the catheter 28 and the waveguides 32, 34, 36 and 38 each have a cylindrical shape, it should be understood that other shapes are possible for the body 22, the catheter 28 and/or the waveguides 32, 34, 36 and 38. For example, the catheter 28 may have a hexagonal cross-sectional shape. The mechanical waveguides 32, 34, 36 may have a cross-sectional hexagonal or triangular shape.

Figure 3:
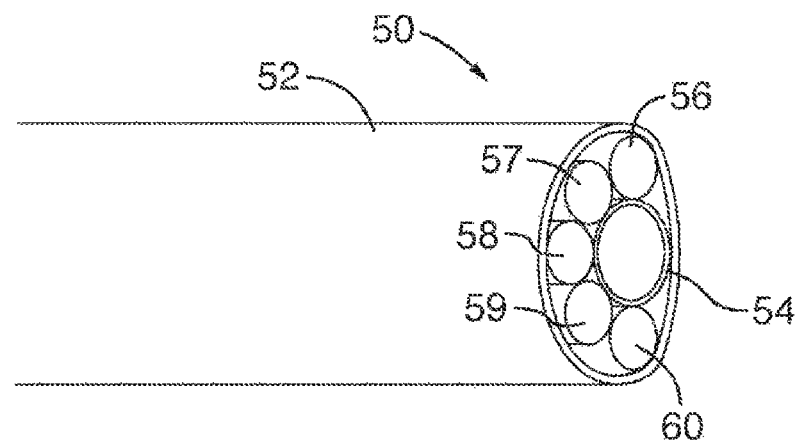
FIG. 3 illustrates a catheter device comprising a sheath, a central catheter and five mechanical waveguides inserted between the sheath and the catheter and arranged asymmetrically around the circumference of the central catheter, in accordance with an embodiment.

While in the illustrated embodiment, the waveguides 32, 34, 36 and 38 are positioned to be symmetrically distributed around the catheter 28, it should be understood that the position of the waveguides 32, 34, 36 and 38 relative to the catheter 28 may vary. FIG. 3 illustrates a catheter device 50 comprising an elongated and hollow body or sleeve 52 in which a catheter 54 and five mechanical waveguides 56, 57, 58, 59 and 60 are inserted. The five mechanical waveguides 56, 57, 58, 59 and 60 are inserted between the body 52 and the catheter 56 so that two adjacent mechanical waveguides 56, 57, 58, 59 and 60 be in physical contact together. In the illustrated embodiment, the mechanical waveguides are positioned around about half of the circumference of the catheter 54.

Figure 4:
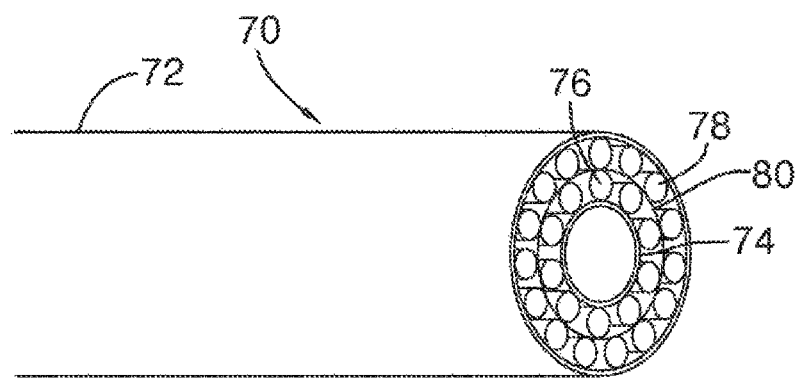
FIG. 4 illustrates a catheter device comprising a sheath, a central catheter and two rows of mechanical waveguides inserted between the sheath and the catheter, in accordance with an embodiment.

While in the above described embodiments the catheter devices 20 and 50 comprise a single layer of mechanical waveguides, it should be understood that the mechanical waveguides may be arranged to form more than one layer. FIG. 4 illustrates one embodiment of a catheter device 70 which comprises two rows or layers of mechanical waveguides. The catheter device 70 comprises an elongated and hollow body or sleeve 72, a concentrically positioned catheter 74, a first row of mechanical waveguides 76 and a second row of mechanical waveguides 78. The first row of mechanical waveguides 76 is positioned between the central catheter 74 and the internal face of the body 72 while the second row of mechanical waveguides 78 is positioned between the first row of mechanical waveguides 76 and the internal face of the body 72.

The mechanical waveguides 76 of the first row may be evenly distributed around the circumference of the catheter 74 and in physical contact with the catheter 74. Adjacent waveguides 76 may be in physical contact together or spaced apart from one another to avoid coupling between adjacent waveguides 76. The mechanical waveguides 78 of the second row may be evenly distributed around the circumference of the first row of mechanical waveguides 76. Adjacent waveguides 78 may be in physical contact together or spaced apart from one another to avoid coupling between adjacent waveguides 78.

In one embodiment, the waveguides 76 are in physical contact with the waveguides 78. In another embodiment and as illustrated in FIG. 4, the catheter device 70 further comprises an elongated and hollow body or sleeve 80 which is inserted between and the first and second rows of mechanical waveguides. The diameter of the hollow body 80 may be equal to the summation of the external diameter of the catheter 74 and twice the diameter of the mechanical waveguide 76. In one embodiment, the body 80 may be a sheath made of an acoustically insulating material to isolate the first row of mechanical waveguides 76 from the second row of mechanical waveguides 78.

Figure 5:
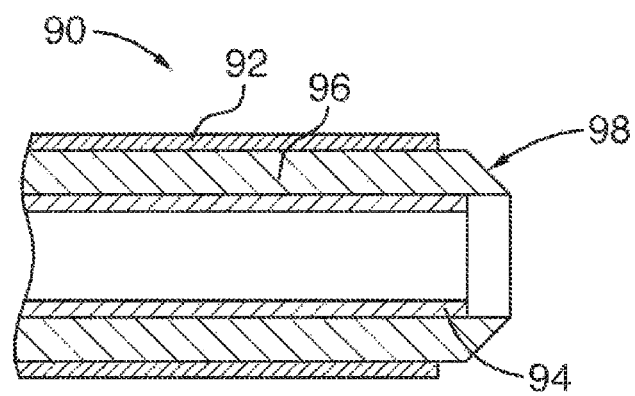
FIG. 5 is a cross-sectional view of a catheter device comprising two mechanical waveguides having a beveled distal end, in accordance with an embodiment.

While in the above-described embodiments the distal end of the mechanical waveguides is planar and right-angled, i.e. the surface of the distal end is orthogonal to the longitudinal axis along which the mechanical waveguide extends, it should be understood that other configurations are possible. For example, FIG. 5 illustrates the cross-section of a catheter device 90 which comprises an elongated and hollow body or sleeve 92, a centrally positioned catheter 94 and two mechanical waveguides 96 inserted between the hollow body 92 and the catheter 94. The distal end 98 of the mechanical waveguides 96 is beveled so that the plane in which the distal end 98 extends intersects the longitudinal axis along which the mechanical waveguide 96 extends at an angle other than 90 degrees. Such a beveled end 98 may facilitate penetration into the target tissue to be treated.

In one embodiment, the mechanical waveguides have a fixed position relative to the catheter 28, 54, 74, 94 and/or the external body 22, 52, 72, 92. In another embodiment, the mechanical waveguides may be adapted to longitudinally move relative to the external body and/or the internal catheter. For example, a mechanical waveguide may be movable relative to the external body and the internal catheter between a retracted position and an extended position. When a mechanical waveguide is in the retracted position, the distal end of the mechanical waveguide may be coplanar with the distal end of the external body and/or the distal end of the catheter. Alternatively, the distal end of the mechanical waveguide may be located between the distal and proximal ends of the external body when the mechanical waveguide is in the retracted position. When the mechanical waveguide is moved longitudinally and in a forward direction relative to the external body and the internal catheter, the distal end of the mechanical waveguide reaches the extended position. In the extended position, the distal end of the mechanical waveguide is in a forward position relative to the position of the distal end of the external body and projects from the distal end of the external body.

In an embodiment in which a mechanical waveguide is movable relative to the external body, the distal end of the mechanical waveguide moves along a straight line, i.e., along the longitudinal axis along which the mechanical waveguide extends. This can be accomplished by moving a mechanical waveguide respective to a stationary sheath, by moving a sheath respective to a stationary mechanical waveguide or a combination thereof.

In another embodiment, the distal end of the mechanical waveguide may follow a curved line when the mechanical waveguide is pushed and moves forward relative to the external body. FIGS. 6a, 6b and 6c illustrate a catheter device 100 comprising an external body or sleeve 102, an internal catheter 104 being concentrically positioned within the sleeve 102 and four mechanical waveguides 106 which are inserted between the internal catheter and the external sleeve and evenly distributed around the circumference of the internal catheter 104.

FIG. 6b illustrates an end view of the mechanical waveguides 106 when in a retracted position. When in this position, the distal end of the mechanical waveguides 106 is coplanar with the distal end of the external sleeve and the internal catheter and the distance between the distal ends of the mechanical waveguides 106 is minimal. FIG. 6c illustrates an end view of the mechanical waveguides 106 when in the extended position, i.e. when the mechanical waveguides 106 are pushed forward relative to the sleeve 102. In this configuration, the distance between the distal ends of the mechanical waveguides 106 is maximal. While the mechanical waveguides 106 are moved forward, the distal end of the mechanical waveguides 106 moves forwardly away from the distal end of the sleeve 102 and radially away the symmetry axis of the catheter 104. In this embodiment, the motion of the distal end of the mechanical waveguides 106 is symmetrical relative to the symmetry axis of the catheter 104.

FIGS. 7a, 7b and 7c illustrate a further embodiment of a catheter device in which mechanical waveguides move non-linearly. The catheter device 120 comprises an external sleeve or body 122, an internal catheter 124 being concentrically positioned within the sleeve 122 and four mechanical waveguides 126 which are inserted between the internal catheter and the external sleeve and evenly distributed around the circumference of the internal catheter 124.

FIG. 7b illustrates and end view of the mechanical waveguides 126 when in a retracted position. When in this position, the distal end of the mechanical waveguides 126 is coplanar with the distal end of the external sleeve and the internal catheter and the distance between the distal ends of the mechanical waveguides 106 is maximal. FIG. 7c illustrates an end view of the mechanical waveguides 126 when in the extended position, i.e. when the mechanical waveguides 126 are pushed forward relative to the sleeve 122. In this configuration, the distance between the distal ends of the mechanical waveguides 106 is minimal. While the mechanical waveguides 126 are moved forward, the distal end of the mechanical waveguides 106 moves forwardly away from the distal end of the sleeve 102 and laterally in a same direction.

It should be understood that any adequate method or device to move the mechanical waveguides radially or laterally as illustrated in FIGS. 6a-6c and 7a-7c may be used. For example, the mechanical waveguides may have a curved shape when in a natural state, i.e., when no force or constraint is applied thereto. In this case, FIGS. 6c and 7c illustrate the waveguides 106 and 126, respectively, in their natural state. By retracting or pulling the waveguides 106 and 126 backward towards the distal end of the sleeve or body, or by pushing the sleeve or body forward towards the distal tip of the waveguides, the mechanical waveguides are completely inserted in the sleeve and adopt a straight shape.

In another example, a naturally curved rod may be secured to each mechanical waveguide so that the portion of the mechanical waveguides that extends outside of the sleeve has a curved shape. By pulling backward the mechanical waveguides, or by pushing the sleeve forward towards the distal tip of the waveguides, the rods are deformed so that the mechanical waveguides may have a straight shape and extend along a straight longitudinal axis.

In a further example, the catheter device may further comprise an extension device for each or a combination of mechanical waveguides. The extension device is adapted to push the distal end of the mechanical waveguide laterally or radially while the mechanical waveguide is forwardly away from the distal end of the sleeve. For example, the extension device may have a structure substantially identical to an umbrella arm. In another example the extension device may comprise an inclined plane whose axial translation may push the distal end of the mechanical waveguide laterally or radially. This inclined plane may be axisymmetric and partially or totally span the circumference of the device such as to push a plurality of mechanical waveguides laterally or radially. In both examples of extension devices, a mechanical element may be used to connect the proximal end of the catheter device to the extension device such as to allow an operator to push one or more mechanical waveguides laterally or radially. In another example the extension device may comprise an inflatable structure, whose inflation fluid (liquid or gas) may be supplied at the proximal end of the catheter device and delivered to the distal end.

It should be understood that the number, position, shape, and dimensions of the mechanical waveguides 32, 34, 36, 38, 56, 76, 78, 96, 106, 126 may vary and be chosen as a function of a desired energy deposition pattern at the distal tip of the catheter device. It should be understood that the mechanical waveguides 32, 34, 36, 38, 56, 76, 78, 96, 106, 126 are made of a material which allows the propagation of mechanical waves. In one embodiment, the mechanical waveguides 306, 326 may be made of titanium.

In another embodiment, the waveguides can be deflected radially or laterally around the catheter to either modify the overall outside diameter of the waveguide bundle or to modify the symmetry of the arrangement as illustrated in FIGS. 6c and 7c.

In one embodiment, the above described catheter device may allow aspiration or blowing from the interstices between the mechanical waveguides. The aspiration could be used to remove debris produced by the catheter device and the blowing of fluid may be used to deliver a fluid such as drugs to the target to be treated.

In one embodiment, the catheter device further comprises tubes extending between the mechanical waveguides for aspiration or blowing purposes.

In one embodiment, the catheter device further comprises tubes extending between the mechanical waveguides to deliver fluid such as drugs to the target to be treated.

In one embodiment, the catheter device may comprise a drug (or similar) capsule at the distal end of the bundle of mechanical waveguides that can be triggered (liberated) from the proximal end with a mechanism running along the length of the catheter device.

In one embodiment, a drug (or similar) capsule may be located at the distal end of the bundle of mechanical waveguides and the capsule can be triggered (liberated) from mechanical waves at the distal end of the device.

In one embodiment, the catheter device further comprises an optical coherence tomography (OCT) or intravascular ultrasound (IVUS) imaging device between the catheter and the sleeve.

In one embodiment, the catheter device is operated in a pulse-echo mode whereby at least one mechanical waveguide is used to transmit a pulse from a pulse generator at its proximal end to a lesion to be treated at its distal end and at least one mechanical waveguide is used to receive the pulse reflected by the lesion, i.e., an echo, and transmit this echo from its distal end buck to its proximal end where the echo can be measured and analyzed to determine the mechanical properties of the lesion from which the echo is received. The mechanical properties of the lesion as obtained from the analyzed echo may then be displayed to the user and optionally used to determine the characteristics of the mechanical pulses to be delivered to the lesion.

In one embodiment, the catheter device is operated in a pulse-echo mode as described above and the analyzed echo is used to tailor the pulse emitted by the pulse generator to the mechanical properties of the lesion to be treated in a closed-loop control method.

In an embodiment in which the catheter device comprises more than one mechanical waveguide, the pulses propagating in the different mechanical waveguides arrive at the distal end of the mechanical waveguides all at the same time, due to the fact that the wave speed and the length of each mechanical waveguide is the same and that the pulses are generated concurrently by the wave generator. In the event that the wave speed may vary from one mechanical waveguide to another, the length of the mechanical waveguides can be adjusted so as to ensure that the pulses concurrently emitted and propagating in different mechanical waveguides arrive at the same time at the distal end of the mechanical waveguides. In another embodiment, the length and/or wave speed of the mechanical waveguides may be adjusted such as to ensure that the mechanical pulses concurrently emitted and propagating in different mechanical waveguides arrive at the distal end of the mechanical waveguides with a pre-determined delay between each mechanical waveguide.

In one embodiment, the size, shape and/or material composition of at least two mechanical waveguides may be different to tailor the flexibility of the catheter device. In one embodiment, the size, shape and/or material composition of at least two mechanical waveguides may be different along their length to tailor the flexibility of the catheter device along its length. For example, a first mechanical waveguide may have a constant diameter along its entire length while a second mechanical waveguide may comprise a first section having a first diameter and a second section having a second and different diameter.

In an embodiment in which the catheter device comprises at least two mechanical waveguides, the catheter device may be connectable to more than one wave generator. Each wave generator is then connected to the distal end of at least one mechanical waveguide. For example, the proximal end of each mechanical waveguide may be connected to a respective wave generator so that each wave generator is connected to a single mechanical waveguide.

In one embodiment, a radio-opaque marker may be attached to the distal end of the catheter device.

In one embodiment, the catheter device may comprise a single mechanical waveguide connected at its proximal end to a pulse generator. At a point along its length away from its proximal end, the mechanical waveguide splits into at least two mechanical waveguides which each extend up to the distal end of the catheter device and may be arranged into the catheter device as described above. It should be understood that the catheter device may comprise more than one mechanical waveguide which each splits into at least two mechanical waveguides. The proximal end of each mechanical waveguide is connectable to a respective wave generator.

In one embodiment, the catheter device may comprise a side lumen connecting with the lumen of the inside catheter at some distance from its distal end, allowing guidewire insertion in a rapid-exchange configuration.

In one embodiment, the distal end of at least two mechanical waveguides may be joined together by welding, brazing, soldering, gluing or any other adequate fastening method. In one embodiment, the distal ends of the mechanical waveguides are joined together forming a donut-like structure at the distal end of the catheter device.

In one embodiment, the catheter device may be covered with a hydrophilic or hydrophobic or friction reducing coating, or a combination thereof.

In one embodiment, the above-described catheter device may be used to treat both calcified and fibrotic lesions while minimizing arterial wall tissue injury and emboli size.

While in the above description, the catheter device comprises a catheter such as the catheter 28, 54, 74, 94, 104 or 124, it should be understood that the catheter may be omitted. In this case, the guiding wire is introduced into the external sleeve between the mechanical waveguide(s) and the internal surface of the sleeve or in the opening created at the center of the bundle of mechanical waveguides.

In the following, there is presented a catheter device which comprises a central catheter and a plurality of annular disks projecting radially and outwardly from the external surface of the central catheter. The annular disks are each provided with a plurality of waveguide receiving apertures for removably or permanently securing mechanical waveguides to the central catheter.

Figure 8:
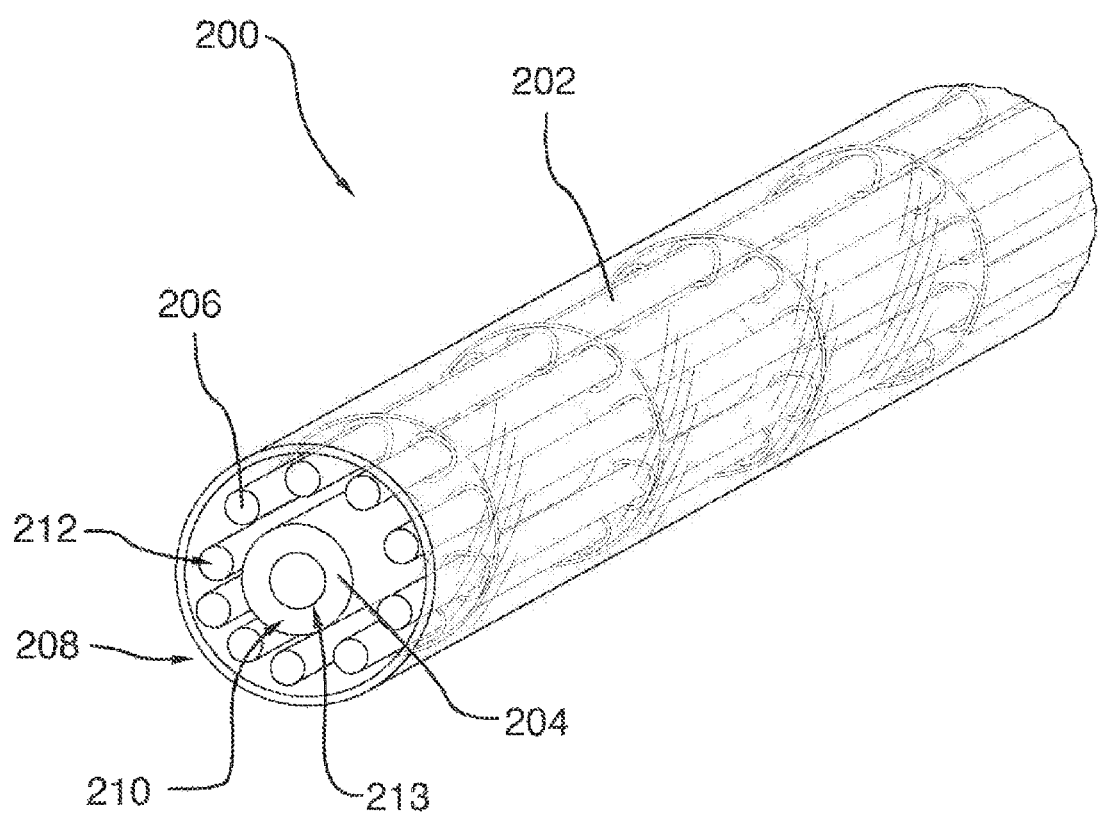
FIG. 8 illustrates a catheter device comprising a catheter provided with a plurality of plates and a sleeve, in accordance with an embodiment.

FIG. 8 illustrates one embodiment of a catheter 200 device which may be used as a transmission member such as the transmission member 16 of FIG. 1 for propagating mechanical waves or pulses coming from an extracorporeal mechanical energy source.

The catheter device 200 comprises a first elongated and hollow body or sleeve 202, a second elongated and hollow body or catheter 204 and a plurality of mechanical waveguides 206. The sleeve 202 extends between a distal end 208 and a proximal end (not shown) along a longitudinal axis. Similarly, the catheter 204 extends between a distal end 210 and a proximal end (not shown) along a longitudinal axis. Each mechanical waveguide 206 also extends longitudinally between a proximal end (not shown) and a distal end 212 along a longitudinal axis. The catheter 204 is provided with a central aperture 213 which extends from the proximal end to the distal end 210 thereof to receive a guidewire therein. A guidewire is used for guiding the catheter device 200 within a blood vessel of a patient and positioning the distal end of the catheter device 200 at an adequate position relative to a lesion to be treated.

Figure 9:
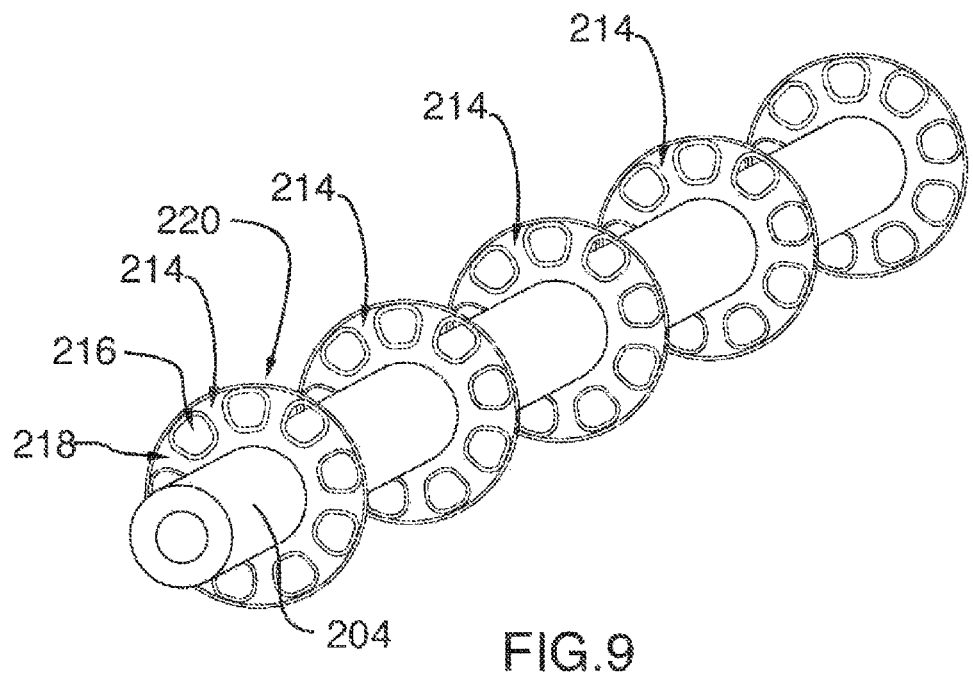
FIG. 9 illustrates the catheter provided with the plurality of plates of FIG. 2, in accordance with an embodiment.

As illustrated in FIG. 9, the catheter device 200 further comprises a plurality of plates 214 which each project radially and outwardly from the external face of the catheter 204 at different locations along the longitudinal axis thereof. In one embodiment, the plates 214 are evenly spaced apart along the catheter 204.

In the illustrated embodiment, the elements of the catheter device 200 have a circular cross-section, i.e., the sleeve 202 and the catheter 204 each have a tubular shape, the mechanical waveguides 206 each have cylindrical shape and the plates 214 each have an annular disk shape. The plates 214 each project radially and outwardly from the external face of the catheter 204 within a plane which is substantially orthogonal to the longitudinal axis of the catheter 204. Each plate 214 extends along the whole circumference of the external face of the catheter 204 to form an annular disk having an aperture in which the catheter 204 is inserted. The external diameter of each plate 214 substantially corresponds to the internal diameter of the sleeve 202.

Furthermore, each plate 214 is provided with a plurality of apertures 216 which each extend through its thickness from a distal end 218 thereof to a proximal end 220. The apertures 216 are located at different angular locations along the circumference of the plate 214. In the illustrated embodiment, the apertures 216 are evenly distributed around the circumference of the plate 214. However, the person skilled in the art would understand that other configurations are possible.

For each aperture 216 of a given plate 214 corresponds a respective aperture 216 of each other plate to form a group of aligned apertures 216. Each aperture 216 of a same group receives the same mechanical waveguide 206 therein. In the illustrated embodiment all corresponding apertures 216 within a group of aligned apertures 216 have the same angular position on their respective plate 214 so that the centers of the corresponding apertures 216 within a same group are aligned along a same longitudinal axis which is parallel to the longitudinal axis of the catheter 204. However, the person skilled in the art will understand that other configurations may be possible. For example, the apertures 216 of a group of apertures each for receiving a same mechanical waveguide 206 may have different angular positions along the length of the catheter 204 so that the mechanical waveguide 206 once inserted into the apertures 216 has a helicoidal shape around the catheter 204.

Each aperture 216 is sized and shaped for receiving a respective mechanical waveguide 206 therein. As illustrated in FIGS. 8 and 9, the catheter device 200 comprises nine mechanical waveguides 206 and each plate 214 comprises nine apertures 216, each for receiving a respective mechanical waveguide 206. As described above, each one of the nine apertures 216 of a given plate 214 is associated with a respective aperture 216 of all other plates 214 to a form a group of aligned apertures for receiving a respective one of the nine mechanical waveguides 206.

It should be understood that the number of plates 214, the number of apertures 216 within a plate 214 and the number of mechanical waveguides 206 may vary as long as the catheter device 200 comprises at least one plate 214, at least one aperture 216 per plate 214 and at least one mechanical waveguide 206 to be inserted into the at least one aperture 216.

In one embodiment, the plates 214 and their apertures 216 for receiving the waveguides 206 therein are used for preventing any physical contact between the mechanical waveguides 206 themselves, between the mechanical waveguides 206 and the catheter 24 and/or between the mechanical waveguides 206 and the sleeve 202 in order to at least limit or reduce coupling losses for the mechanical waves propagating into the mechanical waveguides 206.

Once each waveguide 206 has been inserted into its respective group of apertures 216, the mechanical waveguides 206 are parallel together and radially positioned around the catheter 204. The sleeve 202 is then positioned over the plates 214 so that the sleeve 202 covers the catheter 204 and the waveguides 206. In one embodiment, the length of the sleeve 202 is substantially equal to that of the catheter 204 so that the sleeve 202 covers the whole catheter 204. In another embodiment, the length of the sleeve 202 is shorter than that of the catheter 204. For example, the length of the sleeve 202 may only cover the distal portion of the catheter 204 to be introduced into the patient body.

In one embodiment, the mechanical waveguides 206 are positioned relative to the catheter 204 so that the distal end 212 of the mechanical waveguides 206 is coplanar with the distal end 210 of the catheter 204. In another embodiment, the mechanical waveguides 206 are in a retracted position relative to the distal end 210 of the catheter 204, i.e., the distal end 212 of the mechanical waveguides 206 is positioned between the distal end 210 and the proximal end of the catheter 204. In a further embodiment, the mechanical waveguides 206 are in a forward position relative to the distal end 210 of the catheter 204, i.e., the distal end 210 of the catheter 204 is positioned between the distal end 212 and the proximal end of the mechanical waveguides 206 so that the distal end 212 of the mechanical waveguides 206 project forwardly from the distal end 210 of the catheter 204. In a further example, the distal end 212 of some of the mechanical waveguides 206 may project from the distal end 210 of the catheter 202 while the other mechanical waveguides 206 may have a distal end 212 which is coplanar with the distal end 210 of the catheter 202.

As described above with respect to the catheter device 20, the mechanical waveguides 206 may be movable relative to the catheter 204.

In one embodiment and as described above, the apertures 216 of a same group of apertures may have the same angular position on their respective plate 214. In another embodiment, the angular position of the apertures 216 of a same group may vary from one plate 214 to another to that the longitudinal axis of the mechanical waveguide 26 when inserted into the apertures 216 is not parallel to the longitudinal axis of the catheter 204.

In one embodiment and as illustrated in FIG. 9, the radial position of the apertures 216 of a same group, i.e., the distance between the center of the catheter 204 and the center of an aperture 216 is identical. In another embodiment, the radial position of the apertures 216 of a same group of apertures may vary from one plate 214 to another to that the longitudinal axis of the mechanical waveguide 206 when inserted into the apertures 216 is not parallel to the longitudinal axis of the catheter 204. For example, the distance between the center of the catheter 204 and the center of the apertures 216 may decrease from proximal plates to distal plates so that the distal end 212 of each mechanical waveguide 206 be in physical contact with the distal end of the catheter 204 and/or be in physical contact with the distal end of its neighbor waveguides 206.

It should be understood that the number and position of the plates 214 may vary. Similarly, the number of the apertures 216 and the number of waveguides 206 may also vary. In one embodiment, the number of apertures 216 for each plate 214 is equal to the number of mechanical waveguides 206 so that, for each plate 214, each aperture 216 receives a respective mechanical waveguide 206 therein. In another embodiment, the number of apertures 216 per plate 214 may be greater than the number of mechanical waveguides 206. In this case, at least one group of apertures 216 does not receive a mechanical waveguide 206. In another embodiment, the number of mechanical waveguides 206 may be greater than the number of apertures 214 so that at least one group of aligned apertures may be sized and shaped to receive more than one mechanical waveguide 206 therein.

While the apertures 216 of a same plate 214 have the same shape and size, the person skilled in the art will understand that the shape and/or size of the apertures 216 of a same plate may vary amongst the apertures 216 to receive mechanical waveguides having different shape and/or size for example.

In one embodiment, the spacing or longitudinal distance between adjacent plates 214 along the length of the catheter 204 is chosen to ensure that each mechanical waveguide 206 cannot be in physical contact with the catheter 204, the sleeve 202 or any other mechanical waveguides 206 and to provide a predetermined constant flexural rigidity for the catheter device 200 along its longitudinal axis. The spacing between adjacent plates 214 may be constant along the length of the catheter 204 or may vary.

In one embodiment, the plates 214 are integral with the catheter 204. In this case, the plates 214 correspond to protrusions which project from the catheter 204. In another embodiment, the plates 214 are independent from catheter 204 and subsequently secured to the external face of the catheter 204. In this case, the plates 214 may each have the shape of an annular disk such as the disk 220 illustrated in FIG. 10. The disk 220 is provided with a central aperture 222 of which the shape and size are chosen to correspond to the shape and size of the external face of the catheter 204 to snuggingly fit onto the external face of the catheter 204. The disk 220 is then inserted over the external face of the catheter 204 at a desired longitudinal position along the length of the catheter 204 and fixedly secured thereto. It should be understood that any adequate method for fixedly securing the disks 220 to the catheter 204 may be used. For example, the disks 220 may be secured to the catheter 204 by press fit, heat shrink, appropriate adhesive and/or the like. In another embodiment, the catheter 200, the mechanical waveguides 206 and the disks 220 are maintained in position into the sleeve 202 via compression forces. In a further embodiment, the catheter 204 may comprise a pair or bumps or protrusions for each disk 220 for securing each disk 220 to the catheter 204. The distance between two protrusions or bumps of a same pair is substantially equal to the width of the disk 220 or may be slightly larger than the width of the disk 220. Each disk 220 is inserted onto the catheter 204 between its two corresponding bumps or protrusions which limit the longitudinal movement of the disk 220 relative to the catheter 204. In one embodiment, a disk 220 is first positioned over the catheter 204 at a desired position and then the protrusions are created on the catheter on each side of the disk 220. In another embodiment, the bumps or protrusions are first created on the catheter 204 each at an adequate position and the diameter of the central aperture 222 of the disk is chosen as a function of the dimension of the bumps so that the disk 220 may be inserted between the two bumps by exerting a force of the disk 220 to pass over a bump.

While the plates 214 extend substantially orthogonally from the outer surface of the catheter 204, it should be understood that other configurations may be possible. For example, the plates 214 each may extend in a respective plane that intersects the longitudinal axis of the catheter 204 at an angle other than 90 degrees. While the plates 214 are planar, it should be understood that the plates may be curved for example.

The disk 220 further comprises nine apertures 224 located between the central aperture 222 and the edge 226 of the disk 220. The apertures 224 are evenly distributed around the circumference of the disk 220.

Each aperture 224 has a substantially trapezoidal shape with rounded corners and the dimensions of the aperture 224 are chosen so as to receive a mechanical waveguide 206 therein. In one embodiment, the shape of the apertures 224 is chosen so as to reduce the contact surface area or the number of contact points between the disk 220 and the mechanical waveguide 206 once inserted into the aperture 224. For example, when the mechanical waveguide 206 has a circular cross-section, the aperture 224 may have a square, rectangular or trapezoidal shape so that only four contact points exist between the disk 220 and the mechanical waveguide 206 when inserted into the aperture 224. In another example, the aperture 224 may have a triangular shape so that only three contact points exist between the disk 220 and the cylindrical mechanical waveguide 206 when inserted into the aperture 224.

Figure 10:
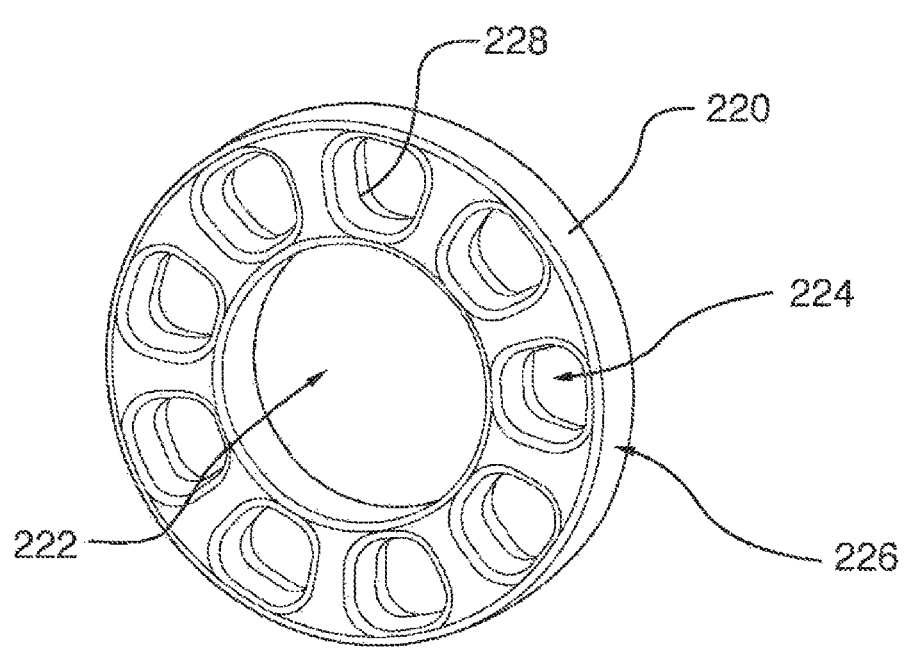
FIG. 10 illustrates a disk-shaped plate, in accordance with an embodiment.

Similarly, the shape of the wall 228 forming and surrounding the aperture 224 may be chosen so as to reduce the contact surface area between the wall 228 and the mechanical waveguide 206 when inserted into the aperture 224. For example and as illustrated in FIG. 10, the wall 228 may be rounded outwardly towards the center of the aperture 224 to reduce the contact surface between the disk 220 and the mechanical waveguide 206. In another embodiment, the wall 228 may have a triangular shape with the apex of the triangle to be in contact with the cylindrical mechanical waveguide 206 in order to reduce the contact surface between the disk 220 and the mechanical waveguide 206.

In one embodiment, the plates 214, 220 are made of a material that is adapted to reduce the coupling of mechanical waves from the mechanical waveguides 206 to the plates 214, 220. For example, the plates 214, 220 may be made of an acoustically insulating material.

While in FIG. 10, the center of the central aperture 222 corresponds to the center of the disk 220, it should be understood that other configurations may be possible. For example, the aperture 222 may not be centrally positioned on the disk 220.

While the apertures 224 are symmetrically and evenly distributed around the circumference of the disk 220, i.e., the angular distance between two adjacent apertures 224 is constant throughout the apertures 224, it should be understood that the apertures 224 may be positioned asymmetrically around the circumference of the disk 220 so that the angular distance between adjacent apertures 224 may vary.

While the distance between the center of the disk 220 and the center of the apertures 224 is constant from one disk 220 to another, it should be understood that other configurations are possible, i.e. the distance between the center of the disk 220 and the center of the apertures 224 may vary from one disk 220 to another.

While the disk 220 comprises a single row of apertures 224, it should be understood that the disk 220 may comprise more than one row of apertures. For example, the disk 220 may comprise a first row of apertures of which the center is positioned at a first distance from the center of the disk 220 and a second row of apertures of which the center is positioned at a second distance from the center of the disk 220, the second distance being greater than the first distance. Each aperture of the first row may be aligned with a respective aperture of the second row, i.e. each aperture of the first row has the same angular position as its corresponding aperture in the second row. Alternatively, the apertures of the first row and the apertures of the second row may not be aligned. In one embodiment, the first row and the second row may comprise the same number of apertures. In another embodiment, the first and second rows of apertures may comprise different numbers of apertures. Similarly, the apertures of the first row may be identical to the apertures of the second row. Alternatively, the apertures of the second row may be different from the apertures of the second rows, e.g. they may have a different shape, dimension, angular positions, and/or the like.

While the central aperture 222 has a circular shape to match that of the catheter 204, it should be understood that other configurations are possible. For example, the central aperture 222 may be square while the catheter 204 is cylindrical.

While the apertures 224 have a shape that is different from that of the cross-section of the mechanical waveguide 206, it should be understood that the apertures 224 may have the same shape as that of the cross-section of the mechanical waveguide 206. For example, the apertures 224 may be circular to receive therein cylindrical mechanical waveguides.

Figure 11A:
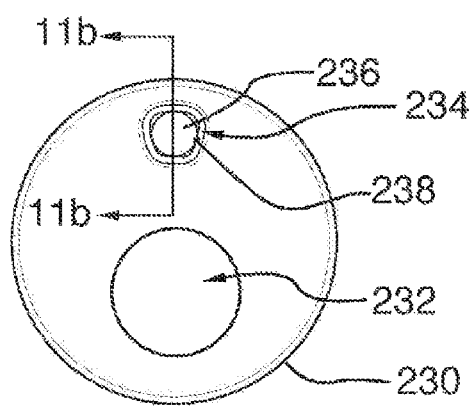
FIG. 11a illustrates a plate provided with a single aperture, in accordance with an embodiment.

FIG. 11a illustrates one embodiment of an annular disk-shaped plate or disk 230 which comprises a catheter receiving aperture 232 which is not centrally positioned within the disk 230. The disk 230 further comprises a rectangular shape aperture 234 adapted to receive a cylindrical mechanical waveguide 236 therein.

Figure 11B:
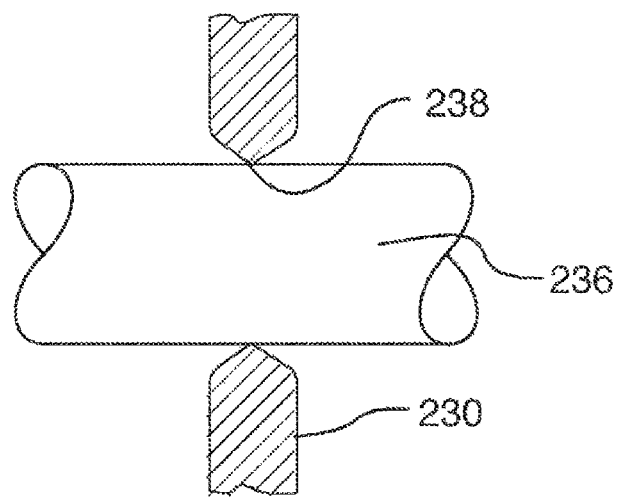

As illustrated in FIG. 11b, the wall forming and surrounding the aperture 234 is rounded so that a single contact point 238 between the mechanical waveguide 236 and the disk 230 exits around the circumference of the mechanical waveguide 236 in order to reduce losses for the mechanical waves propagating in the mechanical waveguide 236.

In one embodiment, the sleeve 202 may be made of a flexible material to correspond to a sheath. In one embodiment, the sleeve 202 may be made of an acoustically insulating material. In one embodiment, the sleeve 202 may be a single or a plurality of smaller diameter wires. Similarly, the catheter 204 may be made of a flexible material. In one embodiment, the catheter 204 may be made of an acoustically insulating material such as a foam.

In one embodiment, the sleeve 202 and/or the catheter 204 is made of a polymer or a graded polymer.

While in the illustrated embodiment the sleeve 202, the catheter 204 and the waveguides 206 each have a cylindrical shape, it should be understood that other shapes are possible. For example, the catheter 204 may have a hexagonal cross-sectional shape. In the same or another example, the mechanical waveguides 206 may have a hexagonal or triangular cross-sectional shape.

While in the above-described embodiments the distal end of the mechanical waveguides 206 is right-angled, i.e., the surface of the distal end 212 is orthogonal to the longitudinal axis along which the mechanical waveguide 206 extends, it should be understood that other configurations are possible. For example the distal end 212 of the mechanical waveguides 206 may be beveled or angled. Such a beveled or angled end 212 may facilitate penetration into the target tissue to be treated. However, the person skilled in the art will understand that other configurations are possible.

It should be understood that the number, position, shape, and dimensions of the mechanical waveguides 206 may be chosen as a function of a desired energy deposition pattern at the distal tip of the catheter device 200. It should be understood that the mechanical waveguides are made of a material which allows the propagation of mechanical waves. In one embodiment, the mechanical waveguides may be made of titanium.

In one embodiment, the section of the catheter 200 adjacent to the distal end 208 thereof is tapered. In this case, the distal end 212 of the mechanical waveguides 206 is in physical contact with the distal end 210 of the catheter 204 and with the sleeve 202. Within the tapered section of the catheter 200, the diameter of the sleeve 202 reduces and the distance between the mechanical waveguides 206 and the catheter 204 also reduces. In one embodiment, the tapered section of the catheter device 200 comprises no plate 214 or disk 220. In another embodiment, the tapered section of the catheter device 200 comprises some plates 214 or disks 220. In this case, the dimensions of the plates 214 or disks 220 reduce to create the tapered shape for the sleeve 202 and the position of the apertures 216 or 224 may be varied to bring the mechanical waveguides 206 closer to the catheter 204.

In one embodiment, the sleeve 202 is made of a heat-shrinkable material to maintain the distal end 212 of the mechanical waveguides 206 in physical contact with the distal end 210 of the catheter 204.

In one embodiment, the catheter device 200 further comprises a ring secured over the distal end of the sleeve 202 to maintain in position the distal end 212 of the mechanical waveguides 206 against the catheter 204. In one embodiment, the ring may be made of a radiopaque material.

In one embodiment, the above described catheter device 200 may allow aspiration or blowing from the interstices between the mechanical waveguides 206. The aspiration could be used to remove debris produced by the catheter device 200 and the blowing of fluid may be used to deliver a fluid such as drugs to the target to be treated.

In one embodiment, the catheter device 200 further comprises tubes extending between the mechanical waveguides for aspiration or blowing purposes. In this case, the disks 220 may comprise further apertures for inserting the aspiration tubes therein. Alternatively, a group of apertures that are not occupied by a mechanical waveguide 206 may be used for receiving the aspiration tube therein.

In one embodiment, the catheter device 200 further comprises at least one tube extending between the mechanical waveguides 206 to deliver fluid such as drugs to the target to be treated. For example, the tube may be inserted into a further group of aligned apertures 216 which are not occupied by a mechanical waveguide 206. In another configuration, a tube may be inserted within a group of apertures in which a mechanical waveguide 206 is already inserted. In this case, the tube is positioned within the apertures 216 between the mechanical waveguide 206 and the wall of the aperture 216.

In one embodiment, the catheter device 200 may comprise a drug (or similar) capsule at the distal end of the bundle of mechanical waveguides 206 that can be triggered (liberated) from the proximal end with a mechanism running along the length of the catheter device 200.

In one embodiment, a drug (or similar) capsule may be located at the distal end of the bundle of mechanical waveguides 206 and the capsule can be triggered (liberated) from mechanical waves at the distal end of the catheter device 200.

In one embodiment, the catheter device 200 further comprises a radiopaque marker. The radiopaque marker may be positioned on the sleeve 202 or on the catheter 204 or on one or more mechanical waveguide 206. In another example, the plate 214 that is adjacent to the distal end of the catheter device 200 may be made of a radiopaque material.

In one embodiment, the catheter device 200 further comprises an optical coherence tomography (OCT) or intravascular ultrasound (IVUS) imaging device between the catheter 24 and the sleeve 22.

In one embodiment, the catheter device 200 may be covered with a hydrophilic or hydrophobic or friction reducing coating, or a combination thereof. For example, the external face of the sleeve 202 may be covered with a hydrophilic or hydrophobic or friction reducing coating, or a combination thereof.

In one embodiment, the above-described catheter device 200 may be used to treat both calcified and fibrotic lesions while minimizing arterial wall tissue injury and emboli size.

In one embodiment, the sleeve 202 may be omitted so that the catheter device 200 only comprises the catheter 204, the disks 220 and the mechanical waveguides 206.

In the following, there is described a further exemplary catheter assembly that may be used a transmission member such as transmission member 16. The catheter assembly comprises a first or central elongated and hollow body hereinafter referred to as a catheter, a plurality of mechanical waveguides surrounding the catheter, an acoustically insulating body positioned on each mechanical waveguide, and a second or external elongated body surrounding the mechanical waveguides and hereinafter referred to as a sleeve. The acoustically insulating bodies allows for acoustically insulating each mechanical waveguide from its surrounding mechanical waveguides and also from the catheter and the sleeve.

Figure 12:
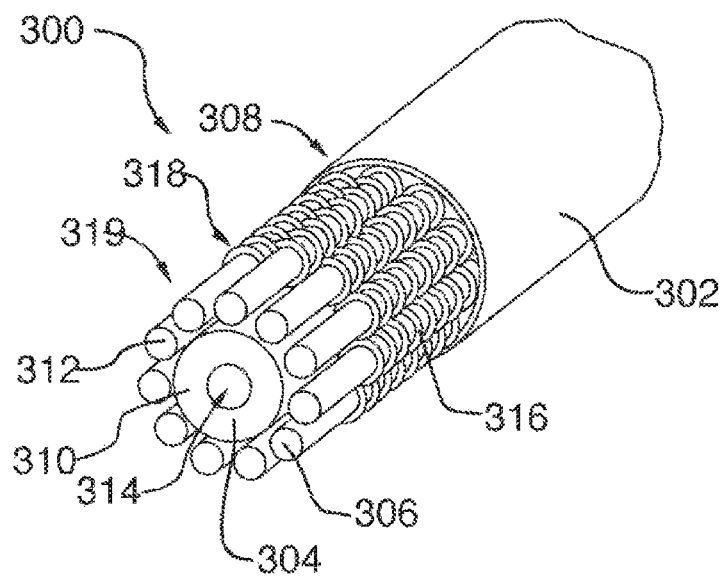
FIG. 12 illustrates a catheter device comprising a central catheter, a plurality of mechanical waveguides each provided with a helical shaped wire, and a tubular sleeve, in accordance with an embodiment.

FIG. 12 illustrates one embodiment of a catheter device 300 which may be used as a transmission member such as the transmission member 16 of FIG. 1 for propagating mechanical waves or pulses or shock waves coming from an extracorporeal mechanical energy source.

The catheter device 300 comprises a first elongated and hollow body or sleeve 302, a second elongated and hollow body or catheter 304 and a plurality of mechanical waveguides 306. The sleeve 302 extends between a distal end 308 and a proximal end (not shown) along a longitudinal axis. Similarly, the catheter 304 extends between a distal end 310 and a proximal end (not shown) along a longitudinal axis. Each mechanical waveguide 306 also extends longitudinally between a proximal end (not shown) and a distal end 312 along a longitudinal axis. The catheter 304 is provided with a central aperture 314 which extends from the proximal end to the distal end 310 thereof to receive a guidewire therein. The guidewire is used for guiding the catheter device 300 within a blood vessel of a patient and positioning the distal end of the catheter device 300 at an adequate position relative to a lesion to be treated.

The catheter device 300 further comprises an acoustically insulating body for each mechanical waveguide 306. Each acoustically insulating body at least partially surrounds its respective mechanical waveguide 306 along at least a portion of the length thereof. Each acoustically insulating body prevents or at least reduces any coupling of the mechanical wave that propagates into its respective mechanical waveguide 306 into the surrounding mechanical waveguides, the catheter 304 and/or the sleeve 302.

In the illustrated embodiment, the acoustically insulating body is in the form of a wire 316 which is wrapped around and along a mechanical waveguide 306 so as to be provided with a helical shape. As result, each helical shaped wire 316 is therefore located between its respective mechanical waveguide 306 and the sleeve 302, the catheter 304 and the surrounding mechanical waveguides 306.

The internal side of each helical shaped wire 316 is in physical contact with its respective mechanical waveguide 306. The external side of each helical shaped wire 316 has at least two contact points: a first contact point with the catheter 304 and a second contact point with the sleeve 302. The external side of each helical shaped wire 316 may have more than two contact points. For example and in addition to the contact points with the catheter 304 and the sleeve 302, the external side of each helical shaped wire 316 may have at least one additional contact point with at least one adjacent mechanical waveguide 306 or with the helical shaped wire 316 of at least one adjacent mechanical waveguide 306. For example, the external side of each helical shaped wire 316 may have a third contact point with either a first adjacent mechanical waveguide 306 or the helical shaped wire 316 of a first adjacent mechanical waveguide 306, and a fourth contact point with either a second adjacent mechanical waveguide 306 or the helical shaped wire 316 of a second adjacent mechanical waveguide 306.

In the illustrated embodiment, the distal end 318 of the helical shaped wire 316 is not aligned with the distal end 312 of its respective mechanical waveguide 306 so that a section 319 of the mechanical waveguide 306 is not covered by the helical shaped wire 316. However, the person skilled in the art would understand that the distal end 318 of the helical shaped wire 316 may be aligned with the distal end 312 of its respective mechanical waveguide 306 so that the whole mechanical waveguide 306 be covered by the helical shaped wire 316.

In one embodiment, the cross-sectional dimension of the helical shaped wire 316 is less than that of the mechanical waveguide 306 around which it is wrapped. If the wires 316 and the mechanical waveguides 306 each have a cylindrical shape, then the diameter of the helical shaped wire 316 is less than that of the mechanical waveguide 306 around which it is wrapped. It should be understood that other configurations may be possible. For example, the diameter of the wires 316 may be substantially equal to that of the mechanical waveguides 306, or be greater than that of the mechanical waveguides 306.

In the illustrated embodiment, each wire 316 is wrapped around its respective mechanical waveguide 306 in a single helical winding having an axial pitch. In one embodiment, the axial pitch is chosen to ensure that each mechanical waveguide 306 cannot be in physical contact with the catheter 304, the sleeve 302 or any other mechanical waveguides 306.

It should be understood that the axial pitch may be chosen to be substantially constant along the length of the mechanical waveguide 306. In one embodiment, the axial pitch of the winding is chosen to be longer than the diameter of the helical shaped wire 316 so that successive windings are not in physical contact with each other. In another embodiment, the axial pitch may vary along the length of the mechanical waveguide 306. For example, the pitch may vary according to a prescribed pattern that ensures that each mechanical waveguide 306 cannot be in physical contact with the catheter 304, the sleeve 302 or any other mechanical waveguides 306 while the catheter device 300 is in actual use and may be curved, for example within tortuous vascular anatomy.

While in the illustrated embodiment, the mechanical waveguides 306 and the helical shaped wires 316 have a circular cross-section, it should be understood that other shapes may be possible. For example, the mechanical waveguides 306 and/or the helical shaped wires 316 may have a square, rectangular, triangular or hexagonal cross-sectional shape. In another example, the mechanical waveguides 306 may each have a square cross-sectional shape while the helical shaped wires 316 may have a circular cross-sectional shape.

While in the illustrated embodiment the helical shaped wire 316 has a cross-section provided with a constant dimension along the length of the mechanical waveguide 306, it should be understood that the dimension of the cross-section of the helical shaped wire 316 may vary along the length of the mechanical waveguide 306. For example, the dimension of the cross-section of the helical shaped wire 316 such as its diameter may decrease from its proximal end to its distal end.

Figure 13:
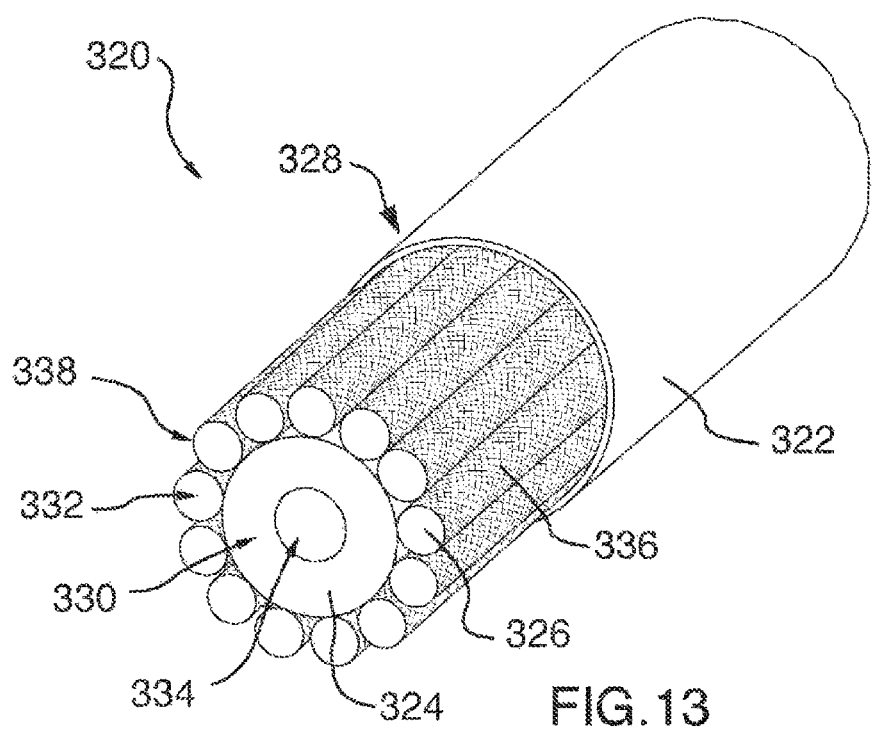
FIG. 13 illustrates a catheter device comprising a central catheter, a plurality of mechanical waveguides each provided with a tubular mesh, and a tubular sleeve, in accordance with an embodiment.

FIG. 13 illustrates another embodiment of a catheter device 320. The catheter device comprises a first elongated and hollow body or sleeve 322, a second elongated and hollow body or catheter 324 and a plurality of mechanical waveguides 326. The sleeve 322 extends between a distal end 328 and a proximal end (not shown) along a longitudinal axis. Similarly, the catheter 324 extends between a distal end 330 and a proximal end (not shown) along a longitudinal axis. Each mechanical waveguide 326 also extends longitudinally between a proximal end (not shown) and a distal end 332 along a longitudinal axis. The catheter 324 is provided with a central aperture 334 which extends from the proximal end to the distal end 330 thereof to receive a guidewire therein.

The catheter device 320 further comprises an acoustically insulating body 336 for each mechanical waveguide 306 and the acoustically insulating body is in the shape of a tubular mesh 336 which is inserted around and along a mechanical waveguide 326. As a result, each tubular mesh 336 is positioned between its respective mechanical waveguide 326 and the sleeve 322, the catheter 324 and the surrounding mechanical waveguides 326 in order to prevent direct physical contact between the respective mechanical waveguide 326 and the sleeve 322, the catheter 324 and the surrounding mechanical waveguides 326.

In the illustrated embodiment, the distal end 338 of the tubular mesh 336 is aligned with the distal end 332 of its respective mechanical waveguide 326 so that the whole mechanical waveguide 326 is covered by the tubular mesh 336. However, the person skilled in the art will understand that the distal end 338 of the tubular mesh 336 may be retracted with respect to the distal end 332 of its respective mechanical waveguide 326 so that a section of the mechanical waveguide 326 may not be covered by the tubular mesh 336.

While in the illustrated embodiment the tubular meshes 336 have a uniform pattern along the length of the mechanical waveguides 326, it should be understood that the pattern of the tubular meshes 336 may vary along the length of the mechanical waveguides 336.

In one embodiment, the thickness of the tubular mesh 336 is substantially constant along the length thereof. In another embodiment, the thickness of the tubular mesh 336 may vary along at least a section thereof.

In one embodiment, the tubular mesh 336 is made from a single material. In another embodiment the tubular mesh 336 is constructed from a plurality of materials.

While in the illustrated embodiments the distal end 308, 328 of the sleeve 302, 322 is not coplanar with the distal end 32, 332 of the mechanical waveguides 306, 326, it should be understood that other configurations may be possible. For example, the sleeve 302, 322 may cover the mechanical waveguides 306, 326 along their whole length up to their distal end 32, 332.

The above-described acoustically insulating bodies, i.e., the helical shaped wires 316 and the tubular mesh 336, are used for preventing any physical contact between the mechanical waveguides 306, 326 themselves, between the mechanical waveguides 306, 326 and the catheter 304, 324 and between the mechanical waveguides 306, 326 and the sleeve 302, 326 in order to prevent or at least limit or reduce coupling losses for the mechanical waves propagating in to the mechanical waveguides 306, 326. The particular shape of the helical shaped wire 316 and that of the tubular mesh 336 allows limiting the contact surface area or number of contact points between the mechanical waveguide 306, 326 and the helical shaped wire 316 or the tubular mesh 336 which allows limiting or minimizing the energy losses from the waveguide 306, 326 to the helical shaped wire 316 or the tubular mesh 336.

While in the illustrated embodiments, each mechanical waveguide 306 is provided with a helical shaped wire 316 and each mechanical waveguide 326 is provided with a tubular mesh 336, it should be understood that only some of the mechanical waveguides 306 may be provided with a helical shaped wire 316 and only some of the mechanical waveguides 326 may be provided with a tubular mesh 336. For example, one over two mechanical waveguides 306 may be provided with a helical shaped wire 316.

In one embodiment, a catheter device may comprise some mechanical waveguides provided with a helical shaped wire 316 while other mechanical waveguides are provided with a tubular mesh 336. In the same or another embodiment, some of the mechanical waveguides may be provided with no helical shaped wire 316 and no tubular mesh 336.

Each helical shaped wire 316 and/or tubular mesh 336 can be wound in place over a waveguide 306, 326. Alternatively, the helical shaped wire 316 and/or the tubular mesh 336 can be pre-formed and thereafter slid or stretched over a mechanical waveguide 306, 326. Once each helical shaped wire 316 and/or tubular mesh 336 is installed over its respective mechanical waveguide 306, 326, each mechanical waveguide 306, 326 is positioned around the catheter 304, 324, and the sleeve 302, 322 is subsequently positioned over the mechanical waveguides 306, 326 so that the sleeve 302, 322 covers the mechanical waveguides 306, 326 along at least a longitudinal section thereof. In one embodiment, the length of the sleeve 302, 322 is substantially equal to that of the catheter 304, 324 so that the sleeve 302, 322 covers the whole catheter 304, 324. In another embodiment, the length of the sleeve 302, 322 is shorter than that of the catheter 304, 324. For example, the sleeve 302, 322 may only cover the portion of the catheter 304, 324 to be introduced into the patient body.

In one embodiment, the mechanical waveguides 306, 326 are positioned relative to the catheter 304, 324 so that the distal end 312, 332 of the mechanical waveguides 306, 326 is coplanar with the distal end 310, 330 of the catheter 304, 324. In another embodiment, the mechanical waveguides 306, 326 are in a retracted position relative to the distal end 310, 330 of the catheter 304, 324, i.e., the distal end 312, 332 of the mechanical waveguides 306, 326 is positioned between the distal end 310, 330 and the proximal end of the catheter 304, 324. In a further embodiment, the mechanical waveguides 306, 326 are in a forward position relative to the distal end 310, 330 of the catheter 304, 324, i.e., the distal end 310, 330 of the catheter 304 is positioned between the distal end 32, 332 and the proximal end of the mechanical waveguides 306, 326 so that the distal end 312, 332 of the mechanical waveguides 306, 326 project forwardly from the distal end 310, 330 of the catheter 304, 324. In a further example, the distal end 312, 332 of some of the mechanical waveguides 306, 326 may project from the distal end 310, 330 of the catheter 302, 322 while the other mechanical waveguides 306, 326 may have a distal end 312, 332 which is coplanar with the distal end 310, 330 of the catheter 302, 332.

In one embodiment, the helical shaped wires 316 and/or the tubular meshes 336 are made of a material or materials that is (are) adapted to reduce the coupling of mechanical waves from the mechanical waveguides 306, 326 to the helical shaped wires 316 and/or the tubular meshes 336. For example, the helical shaped wires 316 and/or the tubular meshes 336 may be made of an acoustically insulating material.

In another embodiment the helical shaped wires 316 and/or the tubular meshes 336 can be made from metal(s) or polymer(s). The diameter, the material and the geometry of helical shaped wires 316 and/or the tubular meshes 336 define the additional flexural and torsional rigidities that each helical shaped wire 316 and/or each tubular mesh 336 imparts to its corresponding mechanical waveguide 306, 326. In one embodiment, the additional flexural and torsional rigidities provided by the helical shaped wire 316 and/or the tubular mesh 336 are small compared to the intrinsic flexural and torsional rigidities of the mechanical waveguide 306, 326, such that there is no stiffening effect from the helical shaped wire 316 or the mesh 336.

In the illustrated embodiments, the elements of the catheter device 300, 320 have a circular cross-section, i.e., the sleeve 302, 322 and the catheter 304, 324 each have a tubular shape and the mechanical waveguides 306, 326 each have cylindrical shape. It should be understood that other shapes are possible. For example, the catheter device 300, 320, the catheter 304, 324 and/or the sleeve 302, 322 may have an elliptical or hexagonal cross-sectional shape.

In the illustrated embodiments, the mechanical waveguides 306, 326 are evenly distributed around the circumference of the catheter 304, 324. However, the person skilled in the art would understand that other configurations are possible as described above.

In the illustrated embodiments, the catheter device 300, 320 is provided with a single layer or row of mechanical waveguides 306, 326 around the circumference of the catheter 304, 324. In another embodiment there may be more than one layer or row of mechanical waveguides 306, 326 around the catheter 304, 324.

Figure 14:
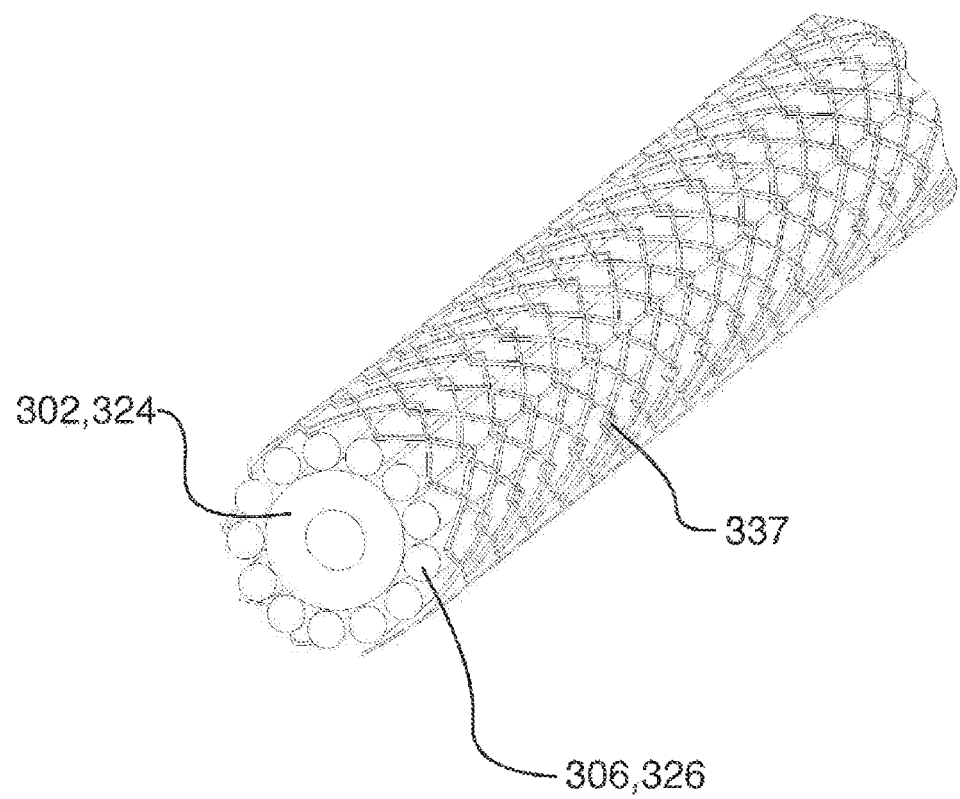
FIG. 14 illustrates a catheter device comprising a central catheter, a plurality of mechanical waveguides, and a mesh sleeve, in accordance with an embodiment.

In one embodiment, the sleeve 302, 322 may be made of a flexible material to correspond to a sheath. In one embodiment, the sleeve 302, 322 may be made of an acoustically insulating material. In one embodiment, the sleeve 302, 322 may be a single or a plurality of smaller diameter wires. In one embodiment, the sleeve 302, 322 may correspond to a tube having a continuous surface. In another embodiment, the sleeve 302, 322 may be a wire mesh 337, as illustrated in FIG. 14.

Similarly, the catheter 304, 324 may be made of a flexible material. In one embodiment, the catheter 304, 324 may be made of an acoustically insulating material.

In one embodiment, the sleeve 302, 322 and/or the catheter 304, 324 is made of a polymer or a graded polymer.

+While in the above-described embodiments, the distal end 312, 332 of the mechanical waveguides 306, 326 is right-angled, i.e., the surface of the distal end 312, 332 is orthogonal to the longitudinal axis along which the mechanical waveguide 306, 326 extends, it should be understood that other configurations are possible. For example the distal end 312, 332 of the mechanical waveguides 306, 326 may be beveled or angled. Such a beveled or angled end 312, 332 may facilitate penetration into the target tissue to be treated. However, the person skilled in the art will understand that other configurations are possible.

It should be understood that the number, position, shape, and dimensions of the mechanical waveguides 306, 326 may be chosen as a function of a desired energy deposition pattern at the distal tip of the catheter device 300, 320. It should be understood that the mechanical waveguides 306, 326 are made of a material which allows the propagation of mechanical waves. In one embodiment, the mechanical waveguides 306, 326 may be made of titanium.

In one embodiment, the section of the catheter device 300, 320 adjacent to the distal end thereof is tapered. In this case, the distal end 312, 332 of the mechanical waveguides 306, 326 may be in physical contact with the distal end 310, 330 of the catheter 304, 324 and with the sleeve 302, 322. Within the tapered section of the catheter 304, 324, the thickness of the helical shaped wires 316 or that of the mesh 336 reduces and the distance between the mechanical waveguides 306, 326 and the catheter 304, 324 also reduces. In one embodiment, the tapered section of the catheter device 300, 320 comprises no helical shaped wires 316 or mesh 336. In another embodiment, the tapered section of the catheter device 300, 320 comprises some helical shaped wires 316 or mesh 336. In this case, the distance between the distal end of each helical shaped wire 316 or mesh 336 and the distal end 310, 330 of the catheter 304, 324 varies from on mechanical waveguide 306, 326 to the next to create the tapered shape for the sleeve 302, 322.

In one embodiment, the sleeve 302, 322 is made of a heat-shrinkable material to maintain the distal end 32, 332 of the mechanical waveguides 306, 326 in physical contact with the distal end 310, 330 of the catheter 304, 324.

In one embodiment, the catheter device 300, 320 further comprises a ring secured over the distal end of the sleeve 302, 322 to maintain in position the distal end 32, 332 of the mechanical waveguides 306, 326 against the catheter 304, 324. In one embodiment, the ring may be made of a radiopaque material.

In one embodiment, the above-described catheter device 300, 320 may allow aspiration or blowing from the interstices between the mechanical waveguides 306, 326, the sleeve 302, 322 and the catheter 304, 324. The aspiration could be used to remove debris produced by the catheter device 300, 320 and the blowing of fluid may be used to deliver a fluid such as drugs to the target to be treated.

In one embodiment, the catheter device 300, 320 further comprises longitudinal tubes extending between the mechanical waveguides for aspiration or blowing purposes.

In one embodiment, the catheter device 300, 320 further comprises at least one longitudinal tube extending between the mechanical waveguides 306, 326 to deliver fluid such as drugs to the target to be treated.

In one embodiment, the catheter device 300, 320 may comprise a drug (or similar) capsule at the distal end of the bundle of mechanical waveguides 306, 326 that can be triggered (liberated) from the proximal end with a mechanism running along the length of the catheter device 300, 320.

In one embodiment, a drug (or similar) capsule may be located at the distal end of the bundle of mechanical waveguides 306, 326 and the capsule can be triggered (liberated) from mechanical waves at the distal end of the catheter device 300, 320.

In one embodiment, the catheter device 300, 320 further comprises a radiopaque marker. The radiopaque marker may be positioned on the sleeve 302, 322 or on the catheter 304, 324 or on one or more mechanical waveguide 306, 326. In another example, the wires 316 or mesh 336 or a portion of the wires 316 or mesh 336 may be made of a radiopaque material.

In one embodiment, the catheter device 300, 320 further comprises an optical coherence tomography (OCT) or intravascular ultrasound (IVUS) imaging device between the catheter 304, 324 and the sleeve 302, 322.

In one embodiment, the wires 316 or mesh 336 comprise at least one optical fiber. In another embodiment, the catheter device 300, 320 comprises at least one optical fiber between the catheter 304, 324 and the sleeve 302, 322.

In one embodiment, the catheter device 300, 320 may be covered with a hydrophilic or hydrophobic or friction reducing coating, or a combination thereof. For example, the external face of the sleeve 302, 322 may be covered with a hydrophilic or hydrophobic or friction reducing coating, or a combination thereof.

In one embodiment, the above-described catheter device 300, 320 may be used to treat both calcified and fibrotic lesions while minimizing arterial wall tissue injury and emboli size.

The person skilled in the art will understand that the different above-described catheter devices may be combined together. For example, at least one of the mechanical waveguides 206 of the catheter device 200 may each be provided with a helical shaped wire 316 or a tubular mesh 336.

The embodiments of the invention described above are intended to be exemplary only. The scope of the invention is therefore intended to be limited solely by the scope of the appended claims.

We claim:

1. A catheter device comprising:
   an internal elongated and hollow body extending between a proximal end and a distal end along a longitudinal axis, the internal elongated and hollow body defining an external surface and a longitudinal aperture that extends between the proximal and distal ends thereof, the longitudinal aperture being shaped and sized for receiving a guide wire therein; and
   at least one mechanical waveguide secured to the external surface of the internal elongated and hollow body and extending longitudinally along at least a portion of the internal elongated and hollow body, the at least one mechanical waveguide for propagating at least one mechanical wave therealong.

2. The catheter device of claim 1, further comprising an external elongated and hollow body defining a cavity, the internal elongated and hollow body and the at least one mechanical waveguide being inserted into the cavity, the at least one mechanical waveguide being positioned between the internal elongated and hollow body and the external elongated and hollow body.

3. The catheter device of claim 2, wherein the external elongated and hollow body is flexible so as to correspond to a sheath.

4. The catheter device of claim 2, wherein at least one of the internal elongated and hollow body and the external elongated and hollow body is made of an acoustically insulating material.

5. The catheter device of claim 2, further comprising at least one tube inserted within the external elongated and hollow body.

6. The catheter device of claim 5, wherein the at least one tube is adapted to blow a fluid at a distal end thereof.

7. The catheter device of claim 5, wherein the at least one tube is adapted to aspirate at least one of a fluid and debris from a distal end thereof.

8. The catheter device of claim 2, wherein the external elongated and hollow body comprises a mesh sleeve.

9. The catheter device of claim 2, further comprising a radiopaque element.

10. The catheter device of claim 1, further comprising at least one plate outwardly projecting from an outer face of the internal elongated and hollow body each at a respective position along a length of the internal elongated and hollow body, each one of the at least one plate comprising at least one waveguide receiving aperture therethrough, each one of the at least one waveguide receiving aperture having a respective one of the at least one mechanical waveguide inserted therein.

11. The catheter device of claim 10, wherein the at least one plate is made of an acoustically insulating material.

12. The catheter device of claim 1, further comprising at least one acoustically insulating body each inserted around a respective one of the at least one mechanical waveguide.

13. The catheter device of claim 12, wherein the at least one acoustically insulating body comprises at least one mesh each inserted around a respective one of the at least one mechanical waveguide.

14. The catheter device of claim 12, wherein the at least one acoustically insulating body extends along at least a longitudinal section of the respective one of the at least one mechanical waveguide.

15. The catheter device of claim 12, wherein the at least one acoustically insulating body is made of an acoustically insulating material.

16. The catheter device of claim 1, wherein a distal end of the at least one mechanical waveguide is movable along the longitudinal axis relative to the distal end of the internal elongated and hollow body.

17. The catheter device of claim 1, wherein the at least one mechanical waveguide comprises a plurality of mechanical waveguides.

18. The catheter device of claim 1, wherein the at least one mechanical waveguide has a distal beveled end.

19. The catheter device of claim 1, wherein a distal end of the at least one mechanical waveguide is coplanar with the distal end of the internal elongated and hollow body.

20. The catheter device of claim 1, wherein a distal end of the at least one mechanical waveguide projects forwardly from the distal end of the internal elongated and hollow body.

21. The catheter device of claim 1, wherein the at least one mechanical waveguide is movable relative to the internal elongated and hollow body.

22. The catheter device of claim 1, further comprising at least one optical fiber.

23. A catheter device comprising:
an internal elongated and hollow body extending between a proximal end and a distal end along a longitudinal axis, the internal elongated and hollow body defining a longitudinal aperture that extends between the proximal and distal ends thereof, the longitudinal aperture being shaped and sized for receiving a guide wire therein;
at least one mechanical waveguide secured to the internal elongated and hollow body and extending longitudinally along at least a portion of the internal elongated and hollow body, the at least one mechanical waveguide for propagating at least one mechanical wave therealong; and
at least one acoustically insulating body each inserted around a respective one of the at least one mechanical waveguide and each comprising at least one wire each wrapped around a respective one of the at least one mechanical waveguide.

24. The catheter device of claim 23, wherein the at least one wire has a helical shape to form a helical winding around the respective one of the at least one mechanical waveguide.

25. The catheter of claim 23, wherein the at least one wire is made of an acoustically insulating material.

26. A catheter device comprising:
an internal elongated and hollow body extending between a proximal end and a distal end along a longitudinal axis, the internal elongated and hollow body defining a longitudinal aperture that extends between the proximal and distal ends thereof, the longitudinal aperture being shaped and sized for receiving a guide wire therein; and
at least one mechanical waveguide secured to the internal elongated and hollow body and extending longitudinally along at least a portion of the internal elongated and hollow body, the at least one mechanical waveguide for propagating at least one mechanical wave therealong;
wherein a distal end of the at least one mechanical waveguide is movable along the longitudinal axis relative to the distal end of the internal elongated and hollow body, and wherein the distal end of the at least one mechanical waveguide is further one of radially and laterally movable relative to a distal end of an external elongated and hollow body.

27. A catheter device comprising:
an internal elongated and hollow body extending between a proximal end and a distal end along a longitudinal axis, the internal elongated and hollow body defining a longitudinal aperture that extends between the proximal and distal ends thereof, the longitudinal aperture being shaped and sized for receiving a guide wire therein;
at least one mechanical waveguide secured to the internal elongated and hollow body and extending longitudinally along at least a portion of the internal elongated and hollow body, the at least one mechanical waveguide for propagating at least one mechanical wave therealong; and
a drug capsule positioned at the distal end of the at least one mechanical waveguide.

\* \* \* \* \*